United States Patent [19]

della Valle

[11] Patent Number: 5,218,094
[45] Date of Patent: Jun. 8, 1993

[54] NEURONOTROPHIC FACTOR DERIVED FROM MAMMALIAN BRAIN TISSUE

[75] Inventor: Francesco della Valle, Padua, Italy

[73] Assignee: Fidia, S.p.A., Abano Terme, Italy

[21] Appl. No.: 562,024

[22] Filed: Aug. 2, 1990

Related U.S. Application Data

[63] Continuation of Ser. No. 153,437, Feb. 8, 1988, abandoned, which is a continuation-in-part of Ser. No. 79,891, Jul. 31, 1987, abandoned.

[30] Foreign Application Priority Data

| Aug. 7, 1986 [IT] | Italy | 48370 A/86 |
|---|---|---|
| Dec. 23, 1986 [IT] | Italy | 48782 A/86 |
| Feb. 8, 1988 [IT] | Italy | 47612 A/88 |

[51] Int. Cl.$^5$ ............ C07K 15/00; A61K 37/02
[52] U.S. Cl. ................ 530/417; 530/327; 530/328; 536/53
[58] Field of Search ......... 530/417, 327, 328; 514/54; 536/53

[56] References Cited

U.S. PATENT DOCUMENTS

4,593,091 6/1986 Della Valle et al. ............ 536/53

FOREIGN PATENT DOCUMENTS

0082612 6/1983 European Pat. Off.
0258111 3/1988 European Pat. Off.

OTHER PUBLICATIONS

Dal Toso et al., INSERM, vol. 126, pp. 297-308, 1984.
dal Toso et al., Molecular aspect of Neurobiology (ed. by Rita Levi, Mont-Lain et al.) Springer-Verlag, Berlin-Heidberg, 1986.
Varon et al., Dev. Neurosciences, vol. 6, pp. 73-100, 1983, 1984.
Marthrope et al., Journal of neuroscience research, vol. 8, pp. 241-250, 1982.
K. J. Anderson et al. Nature, vol. 332, Mar. 24, 1988 pp. 360-361.
R. Dal Toso et al. Journal of Neurochem., vol. 44 (1985) p. 36 Abstract D.
M. Nieto-Sampedro et al. Proc. Natl. Acad. Sci., USA, vol. 81, (1984) Neurobiology, pp. 6250-6254.
P. Walicke et al. Proc. Natl. Acad. Sci., USA, vol. 83, (1986) Neurobiology pp. 3012-3016.
D. Gospodarowicz et al. Proc. Natl. Acad. Sci., USA, vol. 81, (1984) Biochemistry, pp. 6963-6967.
Stedman's Medical Dictionary, 23rd ed., p. 837 "Eagle's Basal M." Condensed Chemical Dictionary, 10th ed., p. 199 "Carbowax".
R. Dal Toso et al. Journal of Neuroscience, vol. 8, No. 3, Mar., 1988, pp. 733-745.
G. Ferrari et al., Neuronal Plasticity and Trophic Factors, FIDIA Research Series in Neuroscience vol. 7, ed. G. Biggio et al. (1988).
R. M. Lindsay et al. Developmental Biology, vol. 112, (1985) pp. 319-328.
S. P. Squinto et al. Cell, vol. 65 (May 31, 1991) pp. 885-893.
Condensed Chemical Dictionary, 10th edit., p. 199.

Primary Examiner—Michael G. Wityshyn
Assistant Examiner—Abdel A. Mohamed
Attorney, Agent, or Firm—Birch, Stewart, Kolasch & Birch

[57] ABSTRACT

A novel neuronotrophic factor having a molecular weight of about 14,000 to 17,000 daltons and an isoelectric point of about 10 is prepared by homogenization of mammalian brain tissue, particularly bovine brain tissue, acid precipitation of the homogenate thus produced, dialysis of the resulting supernatant with dialysis membranes having a molecular weight cut-off of between 5 and 10 kilodaltons and chromatographic fractionation upon molecular weight permeation of the dialyzed supernatant thus produced. The neuronotrophically active fractions may be further purified by cation exchange chromatography with a gradient of ammonium acetate buffer. The neuronotrophic factor of the invention is useful in the treatment of various neuropathological conditions.

19 Claims, 8 Drawing Sheets

NEURONOTROPHIC FACTOR DERIVED FROM MAMMALIAN BRAIN TISSUE

This application is a continuation of copending application Ser. No. 07/153,437 filed on Feb. 8, 1988, now abandoned, which is a continuation-in-part application of Ser. No. 079,891, filed on Jul. 31, 1987, now abandoned.

I. OBJECT

The present invention relates to a new macromolecular neuronotrophic factor designated as SDNF herein, which means stiatal derived neuronotrophic factor) derived from the mammalian brain, in particular from the bovine caudate nucleus, and to a process for preparing the same. From a chemical point of view, the purified neuronotrophic factor is a basic protein with an approximate isoelectric point of 10, the molecular weight of which, determined by electrophoresis with SDS gel, is similar to that of lysozyme, that is to say, about 14,400 daltons. Generally speaking, however, SDNF exhibits a molecular weight ranging from about 14,000 to 17,000 daltons by analysis utilizing SDS-PAGE electrophoresis. From a biological point of view, the molecule is able to enhance in vitro the survival of nervous system neurons in culture, especially those of the central nervous system. The above source, and the chemical and biological characteristics of the neuronotrophic factors are distinguishable from those of other reported identified macromolecular neuronotrophic factors. Furthermore, the pharmaceutical applications of the SDNF molecule have been identified, and these applications form a part of the present invention.

DETAILED DESCRIPTION OF THE INVENTION

Figure 1:
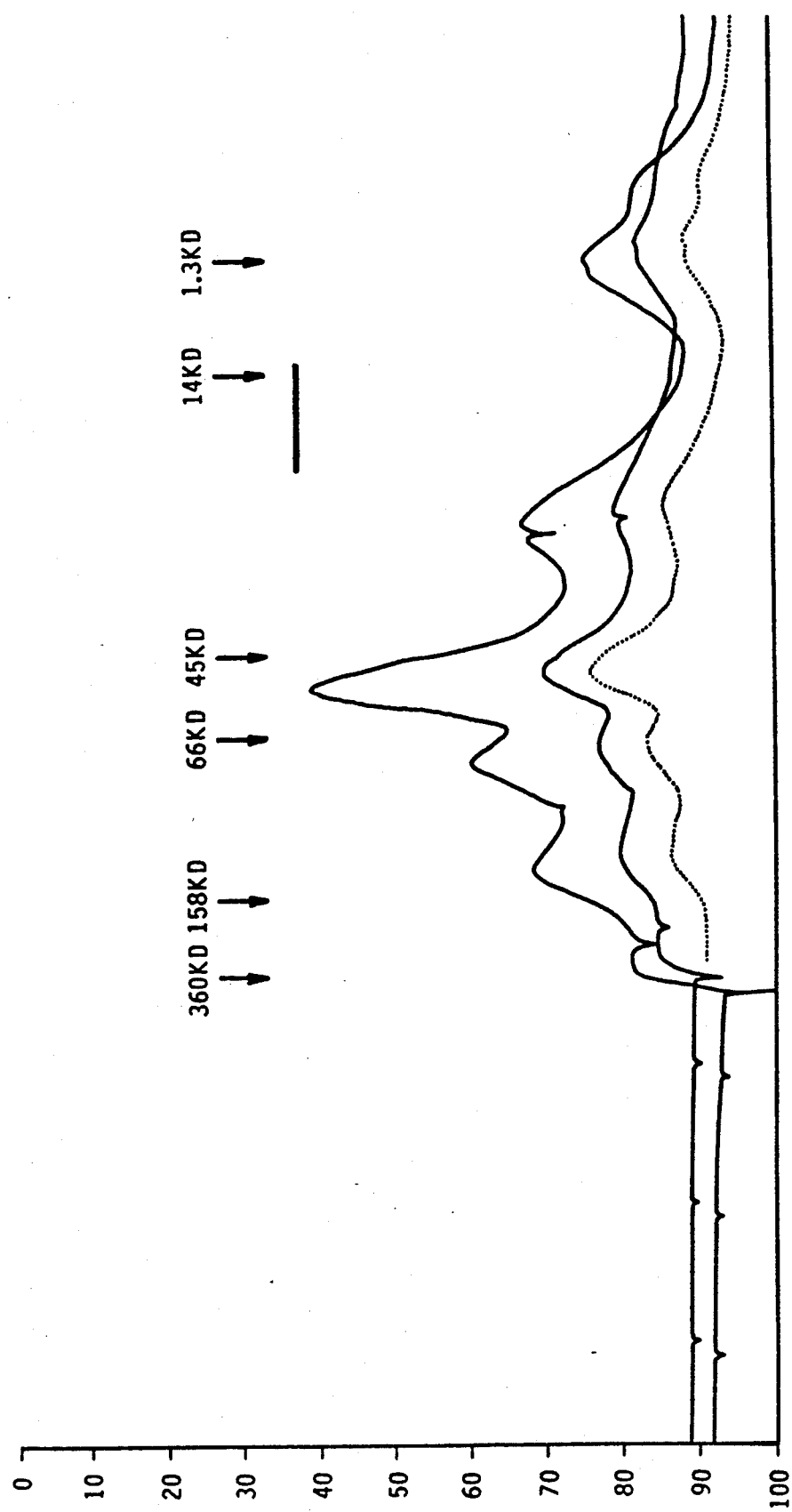
FIG. 1 shows the elution profile of dialyzed bovine caudate supernatent from Sephadex G-150.

II. Introduction a. Definition and Role of the Neuronotrophic factors

It has been ascertained that the survival and growth of mammalian cells in vivo and in vitro are regulated by a series of specific extracellular hormone-like signals, known as growth factors, most of which are proteins or peptides. Biologically, each growth factor acts on one particular group of responsive target cells. Investigation into macromolecular, proteic growth factors, which address survival and neuronal cell growth of mammals both during development and in the adult, is now of considerable interest in the field of neurobiological research. It has been suggested that, during development of the nervous system, extrinsically occurring neuronotrophic factors derived directly from the humoral and cellular microenvironments, regulate survival and death of the neuronal cells (Cowan W. M. et al., Science 225:1258, 1984). Indeed, it has been suggested that the competition between growth innervating axons for target-derived neuronotrophic factors determine which neurons live or die during embryogenesis. In the adult, similar, if not the same, neuronotrophic factors, have been proposed as indispensable to maintain survival of the neuronal cells and to correct functional intracerebral connections (Varon S., Discussions in Neuroscience, vol. II, No. 3, 1985.). Therefore, the progressive weakening and death of neuronal cells (which occur after traumatic lesion, pathological processes such as stroke or neurodegenerative diseases and aging) may involve depletion or inhibition of neuronotrophic factors in vivo (Varon S., ibid; Appel S. H., Ann. Neurol. 10:499 1981; Varon S. et al., Dev. Neurosci. 6:73, 1984 . It has also been suggested by these researchers that adult mammalian neuronotrophic factors are at the root of repair and regenerative processes following lesion not only in the peripheral nervous system, but also in the central nervous system. Indeed, the application of modern neurobiological techniques in transplant and lesion experiments in the central nervous systems of animals has strengthened the belief that neuronal repair is possible in the central nervous system of adult mammals, provided that the right trophic signals are available (Gage F. H. et al., Nature 308:637, 1984). Until recently, the only well-characterized macromolecular proteic neuronotrophic factor was nerve growth factor (NGF) (Levi-Montalcini R. et al., Physiol. Rev. 48:534, 1968; Levi-Montalcini R., Ann. Rev. Neurosci. 5:341, 1982). The finding that NGF was able to stimulate survival only in a limited number of mammalian neuronal types in vitro and in vivo led to the belief that NGF is only one of a family of macromolecular neuronotrophic factors, each one able to regulate the survival of defined neuronal types. At present, only two other macromolecular neuronotrophic factors have been purified and characterized-ciliary neuronotrophic factor (CNTF) (Varon S., Discussions in Neuroscience, vol. II, No. 3, 1985; Varon S. et al., Dev. Neurosci. 6:73, 1984) and brain derived neuronotrophic factor (BDNF) (Varon S., Discussions in Neuroscience, vol. II, No. 3, 1985; Barde Y. et al., Embo J. 1:549, 1982). The reported sources, chemical characteristics and biological activity of these factors are outlined below.

b. Bioassay of Neuronotrophic Factors

In vitro neuronal culture systems have proved to be fundamental and indispensable tools for the study of neuronotrophic activity in tissue extracts and for the monitoring of complex procedures suitable for the fractionation and purification of neuronotrophic factors. It has been demonstrated that mono-layered postmitotic dissociated neuronal cultures kept in vitro in adequately "restrictive" culture conditions necessitate and respond to a trophic support added extrinsically to the culture system. Hence, neuronotrophic activity in semipurified or purified raw preparations may be operatively assessed by monitoring their ability to promote neuronal cell survival in vitro. Furthermore, specific neuronal markers (e.g. analysis of neurofilament content or specific uptake markers) are used to support or confirm the morphological criteria.

c. Characteristics of Identified Neuronotrophic Factors

As noted previously, the macromolecular neuronotrophic factors identified to date are nerve growth factor (NGF), ciliary neuronotrophic factor (CNTF) and brain derived neuronotrophic factor (BDNF). The reported biological sources, chemical characteristics and biological activity of each of these factors are outlined hereafter.

1. Nerve Growth Factor (NGF)

Source: NGF was originally discovered in mouse sarcoma tumors (Levi-Montalcini R. et al., J. Exp. Zool. 116:321, 1951) and was then purified to homogeneity from submandibular salivary glands of male mice (Varon S. et al., Biochemistry 6:2202, 1967) and from snake venom (Angeletti R. H., Proc. Natl. Acad. Sci. USA 65:668, 1970). Many other relatively rich sources of NGF have also been reported, including guinea pig prostate (Harper G. P. et al., Nature 279:160, 1979) and human placenta (Goldstein L. D. et al., Neurochem. Res. 3 175, 1978). Small quantities of NGF have been reported to be present in other tissues including the mammalian central nervous system (Varon S., Discussions in Neuroscience, vol. II, No. 3, 1985; Hefti F. et al., Neuroscience 14:55, 1985). The physiological relationship between these potential sources of NGF and the apparent action sites is not very clear, but it is generally supposed that NGF is secreted from various peripheral tissues requiring innervation by those cells which respond to NGF. The sequence and clonation of NGF obtained from submandibular glands of male mice were also carried out (Scott J. et al., Nature 302:538, 1983; Ulrich A. et al., Nature 303:821, 1983). The human $\beta$-NGF gene has also been successfully isolated and cloned (Ulrich A. et al., Nature 303:821, 1983; European Patent No. 0121388).

Chemical characteristics: NGF obtained from submandibular glands of mice was the type most completely characterized. NGF from mouse glands acts as a 7S proteic complex (molecular weight about 140,000 daltons) of three different subunits ($\alpha$, $\beta$, $\gamma$) including $Zn^+$. The activity of NGF is exclusively associated with the subunit $\beta$ (known as 2.5S NGF), a basic dimeric protein with a molecular weight of about 25,300 daltons (showing a molecular weight of about 12,650 daltons on electrophoresis with gel SDS) the isoelectric point of which is approximately 9.3. The sequences of $\beta$-NGF from submandibular glands of male mice and human provenience or sources have been reported (Scott J. et al., Nature 302:538, 1983; Ulrich A. et al., Nature 303:821, 1983).

Biological activity: NGF from mouse submandibular gland was used for most of the studies on the activity of NGF in vitro and in vivo.

The range of biological activity in vitro of NGF has been determined both on primary neuronal cells and on clonal cells in culture. The primary neuronal cells reported as responding to NGF in vitro include fetal sensorial neurons (embryonic day 8-12) in dorsal root ganglia, autonomic noradrenergic fetal neurons in the sympathetic ganglia, cholinergic fetal neurons in the septum and adrenal chromaffin cells in development. While sensorial and sympathetic neurons depend on NGF for survival and development, cholinergic neurons do not seem to require NGF for survival, but only for their differentiation, that is to say, the expression of characteristic phenotypic traits bound to the neurotransmittor. The addition of NGF to the adrenal chromaffin cells (cells derived from the neural crest) in the initial stage of their development causes the expression of neuronal phenotypes. The clonal cells reported as responding to NGF in vitro include chromaffin adrenal cells derived from tumors of the neural crest known as pheochromocytoma cells (PC12) and human neuroblastoma cells. After treatment with NGF these cells switch from a highly proliferous form of behaviour to a postmitotic neuronal state. The neurons reported as responding in vivo to NGF include sensory neurons of dorsal root ganglia, sympathetic neurons and cholinergic neurons of the central nervous system both during development and in the adult following lesion. In the latter case, intracerebral administration of NGF promoted survival of neuronal cells and expression of characteristic phenotypic traits. These effects are associated with an improvement in lesion-induced behavioural variations.

2. Ciliary Neuronotrophic Factor (CNTF)

Source: The CNTF was first detected and purified from embryonic tissue ($E_8$) from chicks' eyes including the choroid and the ciliary body of the iris together with the pigmentary epithelium. Subsequently, CNTF activity was identified in a variety of different tissue extracts, including the adult rat sciatic nerve and wound fluid from the central nervous system of the rat.

Chemical characteristics: CNTF purified from chick fetus intraocular tissue (yielding approximately $2 \times 10^{-4}$ in terms of protein, 9% in terms of trophic activity) displays on electrophoresis with SDS gel a molecular weight of 20,400 daltons and has an isoelectric point of about 5. This molecular weight, and similarly its negative net charge, clearly differentiate the CNTF from the submandibular protein $\beta$-NGF of the mouse. No sequence of CNTF purified from chicks' eyes has been reported, and neither has purification on a preparative scale of CNTF derived from mammals.

Biological activity: Biological studies have been carried out mainly using extracts derived from chicks' eyes, semipurified or purified preparations of CNTF and in vitro alone. Neurons responding in vitro include ciliary ganglia ($E_8$) from fetal chicks, neurons $E_{10}$ from fetal chick dorsal root ganglia, neonatal neurons from mouse dorsal root ganglia, and sympathetic neurons from chick $E_{11}$ ganglia and rat neonatal ganglia. It has been reported that none of these activities is blocked or inhibited by antibodies to mouse submandibular $\beta$-NGF. No mention has been made of the effects in vivo of CNTF.

3. Brain Derived Neuronotrophic Factor (BDNF)

Source: BDNF activity has been studied both in conditioned media from the C6 rat clonal cell line and in brain extracts of various species. The factor has been purified from adult pig brain.

Chemical characteristics: BDNF purified from adult pig brain (yielding $3.8 \times 10^{-8}$ in terms of protein, less than 5% in terms of trophic activity) is a highly basic polypeptide (pI>10.1) with a molecular weight of about 12,300 daltons on electrophoresis with SDS gel. No sequence has been reported in the literature. The BDNF molecule and its extraction procedure are described in West German Patent DE 3213963 A1.

Biological activity: Studies on biological activity have been carried out using raw extract derived from pig brain, semipurified and purified BDNF preparations and exclusively vitro. It has been shown to promote survival both of sensory neurons derived from the placode and of sensory neurons derived from the neural crest and to promote neurite outgrowth and cell survival of in vitro retina explants (Turner J. E., Develop. Brain Res. 18:251, 1985; Turner J. E., Develop. Brain Res. 18:265, 1985). Although its chemical properties are very similar to those of $\beta$-NGF, no immunological cross-reaction has been detected. Furthermore, BDNF does not act on sympathetic neurons. No in vivo effects of BDNF have been reported.

III. Novel Neuronotrophic Factor Derived from Mammalian Brain

The present invention relates to a novel neuronotrophic factor (SDNF) having a molecular weight ranging from approximately 14,000 to 17,000 daltons which is active on neurons of the nervous system, and to a process for preparing it.

a. Source and Purification Procedure

The novel neuronotrophic factor of the invention may be obtained according to the following procedure which is also part of the present invention. The procedure used is characterized by homogenization of mammalian, preferably bovine, brain and preferably from the caudate nuclei, under neutral conditions, followed by an acid precipitation at pH 4-5 and chromatographic fractionation on a molecular sieve with diluted buffered eluent at a concentration within the range of 10 mM to 30mM; the active fractions are further purified by cation-exchange chromatography with a gradient of between 0.01M and 1M of ammonium acetate buffer and the active fractions are pooled and freeze-dried. Both fresh and frozen (e.g. $-70°$ C.) mammalian brains can be used. All the stages of purification illustrated below are best carried out at a temperature of between $0°$ and $6°$ C. For the preparation of each batch, the whole or partial brains are homogenized in 2 or 4 volumes of buffered solution diluted at a pH varying between 6 and 7.4 and then acidified preferably with HCl at a pH varying between 4 and 5, preferably 4.5, and agitated for several hours. The precipitated material is separated by centrifugation (e.g. 40,000 rpm for 40 minutes), the supernatant neutralized and dialysed against diluted buffered solution and freeze-dried. The dialysis membranes have a molecular cut-off of between 5 and 10 kilodaltons. Fractionation by a molecular filter is carried out using a stationary phase with a fractionation range of between 5,000 and 150,000 daltons. The sample is eluted with buffered solution diluted to a concentration varying between 10 mM and 30 mM and a pH varying between 6 and 7.4. The biologically active fractions are pooled, freeze-dried, applied to a cation-exchange chromatographic column and eluted with a gradient of ammonium acetate buffer of between 0.1M and 1M and a pH of between 6 and 7. The neuronotrophic activity is eluted approximately at 1M and the active fractions once more pooled and freeze-dried. The above procedure may be interrupted at any stage of purification if the biologically active material is already sufficiently pure or if other less purified fractions are to be used. The following example describes the invention, although the invention is not limited to it.

EXAMPLE

Figure 3A:
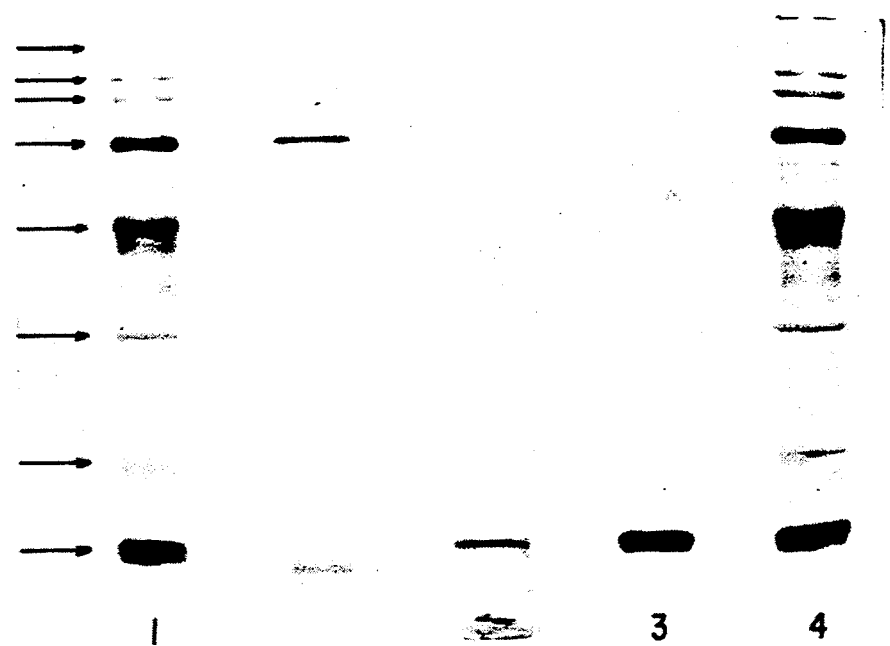
FIG. 3a represents the results of SDS-PAGE gel electrophoresis after silver staining of the active material derived from different stages of the purification procedure as compared to standard proteins.

Fresh bovine brains were obtained from the slaughter house and the caudate nuclei were dissected on ice. For the preparation of each batch approximately 150 g of caudate tissue (25-30 brains) were homogenized (Polytron, setting 6, 60 seconds) in 3 volumes of phosphate buffered saline (PBS) diluted 1:10 (pH 7.4) containing phenylmethylsulfonyl fluoride (PMSF) (0.3 mg/ml) and EGTA (ethyleneglycol-bis-($\beta$-aminoethyl ether-N,N,N',N'-tetraacetic acid) (1 mM), acidified with HCl at pH 4.5, maintained in ice for 2 hours and subsequently centrifuged (40,000 rpm for 40 minutes). The supernatant was pooled, neutralized (pH 7.4), dialysed overnight (cut-off at 8 kDa) in diluted PBS 1:10 (pH 7.4), freeze-dried and kept in aliquots at $-20°$ C. Immediately before use, the aliquots are resuspended in 1/10 of the initial volume using distilled water and the protein content is evaluated according to the method of Peterson G. L. (Anal. Biochem. 83:346, 1977). The samples were then diluted in the culture medium, filtered through 0.45 micron Millex filters presaturated with bovine serum albumin (1 mg/ml), and suitable quantities of the filtered supernatant fraction were added to the serum-free mesencephalic cell cultures to assay the neuronotrophic activity. A Sephadex G-150 (fine) column was used (measuring 8 cm$\times$120 cm) to separate the supernatant components according to their molecular weight. The freeze-dried supernatants were resuspended in distilled water and applied to the column (approximately 750 mg of protein in 6 ml of elution buffer). The elution buffer had the following millimolar composition (pH 7,30): NaCl, 13.68; KCl, 0.27; Na$_2$HPO$_4$.7H$_2$O, 0.8; KH$_2$PO$_4$, 1.5. The column was eluted at a flow of 90 ml per hour, using a peristaltic pump. The optical density of the eluate was continually monitored at 280 nm with a UV monitor. Fractions of 15 ml were automatically gathered and after freeze-drying were tested for neuronotrophic activity. Gel filtration chromatography and fraction collection were carried out in a cold room at $4°$ C. The biologically active fractions eluted from the Sephadex G-150 column were pooled and freeze-dried. Aliquots of the freeze-dried material were resuspended in 110 $\mu$l 0.1M of CH$_3$COO(NH)$_4$, pH 6.45. The proteins were measured in 10 $\mu$l. The remaining 100 $\mu$l (1.9 mg protein) was applied to a TSK-CM-3SW column (an ion exchange column for HPLC). The fractions were eluted with a gradient of (NH$_4$)COOCH$_3$ (0.1M-1M), pH 6.45 at a flow of 0.5 ml per min. Buffer A: 0.1M (NH$_4$)COOCH$_3$, pH 6 45. Buffer B: 1M (NH$_4$)COOCH$_3$, pH 6.45. Profile of the gradient: 0-20 minutes, 100% A/0% B (isocratic); 20-40 minutes, 0% A/100% B (linear); 40-70 minutes, 0% A/100% B (isocratic); 70-75 minutes, 100% A/0% B (linear). The fractions were freeze-dried and resuspended in 0.6 ml of phosphate buffer (10 mM, pH 5.7). The proteins were measured in 100 μl and the remaining material was used for the bioassay and SDS-PAGE analysis. Table 1 summarizes the main stages of the purification procedure and reports an example of the degree of purification (in terms of protein) and the percentage yield of neuronotrophic activity which may be achieved during the purification procedure. The protein and trophic activity yields distinguish this procedure from the other procedures used for the purification of CNTF and BDNF.

tralization and dialysis of the total homogenate on a Sephadex G-150 column and a TSK-CM-3SW column) are shown in FIG. 3A. FIG. 3A shows examples of SDS-PAGE gel electrophoresis after silver staining with BioRad standard proteins (lanes 1 and 5) and active material (5 μg protein/lane) derived from the major stages of the purification procedure, that is, supernatant extract obtained after acid precipitation, neutralization and freeze-drying of the total homogenate (lane 2) and the active eluate of the Sephadex G-150 column (lane 3) and from the TSK-CM-3SW column (lane 4).

TABLE 1

SUMMARY OF THE MAJOR PURIFICATION STAGES OF THE BOVINE BRAIN NEURONOTROPHIC FACTOR

| Stage | Total protein (mg) | Purif. factor | Specific activity μg/TU* | Total TU | TU Recovery % |
|---|---|---|---|---|---|
| Homogenate | 11,625 | 1 | — | — | — |
| Supernat. after acid precipit. | 750 | 15.5 | 6 | 125,000 | 100% |
| Sephadex G-150 | 14.7 | 791 | 0.3 | 49,000 | 39% |
| CM-HPLC | 0.361 | 32202 | 0.01 | 36,100 | 29% |

*The trophic unit (TU) is defined as the protein concentration (in μg/ml) which favours survival of half the maximum number of neurons surviving in response to a saturating concentration of active material.

b. Chemical Characterization

Figure 2:
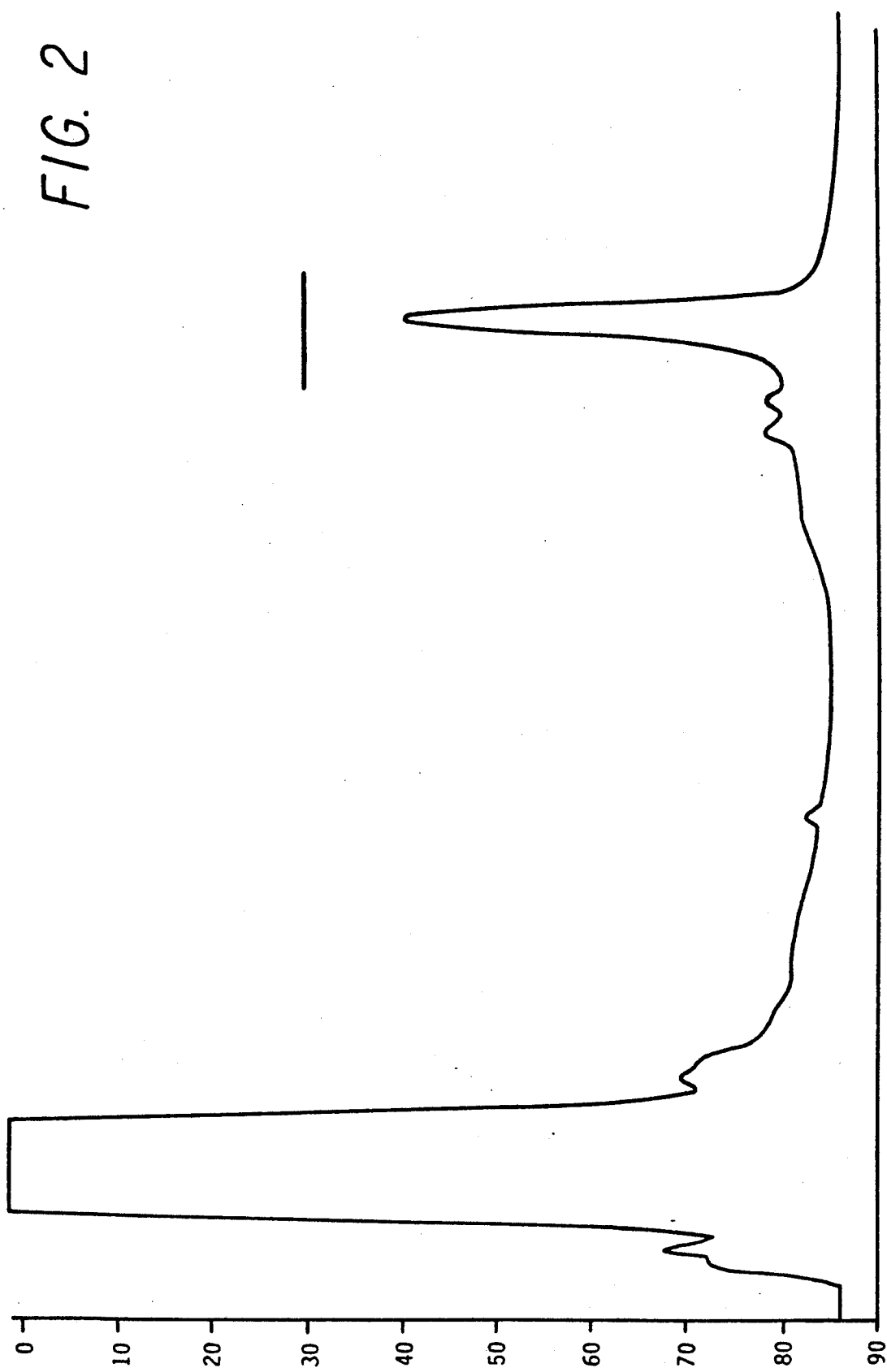
FIG. 2 shows an HPLC elution profile of active eluates obtained from a Sephadex G-150 column.

Biological activity in the raw supernatant fraction obtained from the total homogenate after acid precipitation, neutralization and dialysis, is trypsin-sensitive, indicating that the active molecule is of a proteic or peptidic nature. The biologically active molecule present in the above raw supernatant extract elutes from the Sephadex G-150 column in fractions corresponding to a molecular weight varying between 10,000 and 30,000 daltons (FIG. 1). FIG. 1 shows a typical elution profile from Sephadex G-150 of bovine caudate supernatant obtained after acid precipitation, neutralization and dialysis of the total homogenate together with identification of the biologically active fractions. The conditions of preparation have been described above. All fractions were assayed for biological activity with protein concentrations varying between 0.01 and 10 μg/ml. Activity was observed in the fractions indicated by the horizontal line in FIG. 1. The biologically active molecule present in the active fractions derived from the Sephadex G-150 column elutes from the TSK-CM-3SW column at an ammonium acetate buffer concentration of about 1M (FIG. 2). FIG. 2 shows a typical HPLC elution profile from a TSK-CM-3SW column of active eluates obtained from a Sephadex G-150 column. The conditions of purification are described. All fractions are examined for biological activity with protein concentrations varying between 0.001 and 0.3 μg/ml. Activity represented by the horizontal line was observed in fractions eluted at about 1M of ammonium acetate.

The latter elution time is similar to that of cytochrome C, indicating that the isoelectric point of the active molecule is similar to that of cytochrome C, that is, approximately 10–10.5. This characteristic distinguishes the active molecule from CNTF which has a pI of about 5. SDS-PAGE electrophoresis carried out according to the method of Lee V. et al. (Neuroscience 6:2773, 1981), using 12.5% w/v polyacrylamide slab gels and discontinuous buffer containing SDS according to the method of Laemmli U. K. (Nature 227:680, 1970), of the biologically active material derived from the major steps of the purification procedure (supernatant extract obtained following acid precipitation, neu- The standard molecular weight indicators used were myosin (molecular weight 200,000), β-galactosidase (molecular weight 116,250), phosphorylase b (molecular weight 92,500), bovine serum albumin (molecular weight 66,200), ovalbumin (molecular weight 45,000), carbon anhydrase (molecular weight 31,000), soya bean trypsin inhibitor (molecular weight 21,500), and lysozyme (molecular weight 14,400). The sample buffer for electrophoresis consisted of 62.5 mM of Tris (tri(hydroxymethyl)aminomethane) (pH 6.8), 10% w/v of glycerol, 2% w/v of SDS (sodium dodecyl sulfate), 2.5 mM of EDTA, 2.5 mM of EGTA (ethylene glycol-bis(β-aminothylether-N,N,N',N'-tetraacetic acid)), 0.01% of blue bromophenol and 5% of β-mercaptoethanol.

Figure 3B:
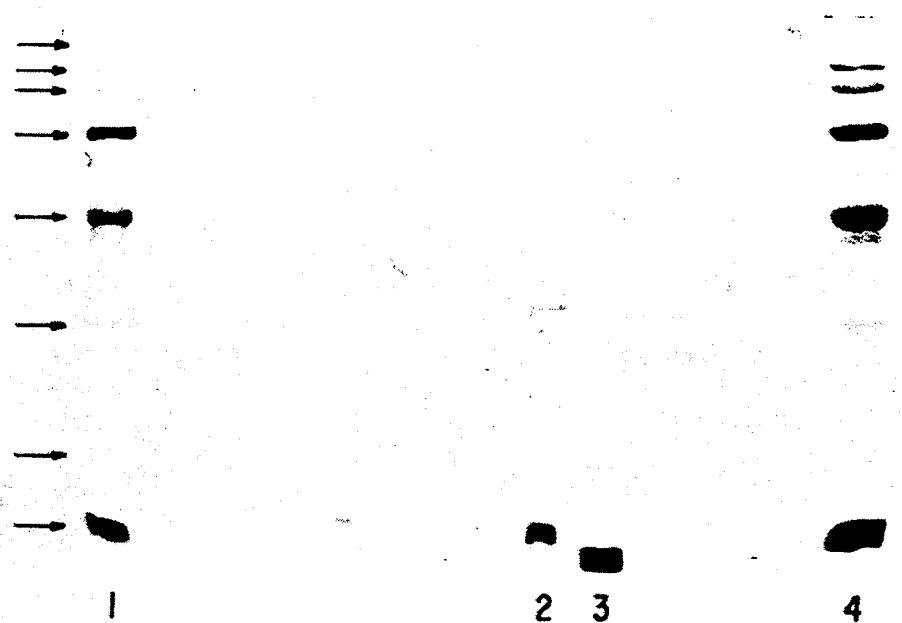
FIG. 3b shows the results of SDS-PAGE gel electrophoresis after silver staining of the active material eulate in comparison to standard indicators and β-NGF from mouse submandibular gland.

The biologically active material obtained from the TSK-CM-3SW column migrates as a single band with a molecular weight similar to that of lysozyme (BioRad) used as standard and having a molecular weight of about 14,400 daltons. This molecular weight distinguishes the active molecule from the other identified neuronotrophic factors (NGF, CNTF, BDNF). Indeed, the active material eluted from the TSK-CM-3SW column does not migrate after SDS-PAGE gel electrophoresis in a position similar to that of β-NGF from mouse salivary glands (FIG. 3B). FIG. 3B illustrates an example of SDS-PAGE gel electrophoresis after silver staining with standard BioRad indicators (lanes 1 and 4), with 2.5 μg of β-NGF from mouse submandibular gland (lane 2) and with 2.5 μg of active material eluted from the TSK-CM-3SW column (lane 3). Standard protein was used as in FIG. 3A.

The NGF migrates to a position below that of the migration of the active molecule eluted from the TSK-CM-3SW column. It has been reported that BDN migrates in SDS electrophoretic movement to a position similar to that of NGF. This further indicates that the active molecule eluted from the TSK-CM-3SW column may be distinct from BDNF.

c. Biological Activity

The biological activity of the material derived from the major passages of the purification procedure (the raw supernatant extract obtained after acid precipitation, neutralization and dialysis of the total homogenate, the eluates obtained from the G-150 column and the eluates obtained from the TSK-CM-3SW column) is usually established by monitoring its effects on survival of dissociated primary mesencephalic cells from fetal mouse kept in serum-free culture. Furthermore, determinations were made of the specific uptake of $^3$H-dopamine in dopaminergic neurons and the specific uptake of $^{14}$C-GABA (GABA means γ-aminobutyric acid) in the GABAergic neurons present in the culture system so as to corroborate or confirm the morphological criteria. Outlined below are the cell culture preparation methods, cell survival evaluation and specific uptake parameters together with the characteristics of cell culture preparation and effects of the material derived from the major stages of the purification procedure.

1. Cell Culture Preparation Method and Immunochemical Criteria Used for the Evaluation of Cell Types In Vitro Rostral mesencephalic tegmentum was dissected under sterile conditions from brains of 13-day embryo mice. The pooled brain areas were mechanically dissociated in PBS with the following millimolar composition: NaCl, 136.8; KCl, 2.7; Na$_7$HPO$_4$.7H$_2$O, 8; KH$_2$PO$_4$, 1.5 and glucose content (6 mg/ml) and bovine serum albumin (0.1 mg/ml) (pH 7.4). The cells were then centrifuged (45 rpm for 4 minutes), resuspended in the culture medium, passed through a 20 μm Nytex filter, counted with an oulter cell counter and plated in 35 mm Falcon tissue culture plastic dishes. Each dish was coated with bovine skin collagen (Vitrogen, 100 μg protein), using Eagle's Basal Medium (BME), NaHCO$_3$ and NaOH so as to raise the ionic strength and pH (Elsdale T. et al., J. Cell Biol. 54:626, 1972). The culture medium consisted of a mixture of BME and Ham's F12 (1:1) supplemented with glucose (33 mM), glutamine (2 mM), NaHCO$_3$ (15 mM), HEPES (N-2-hydroxyethyl-piperazine-N'-2-ethanesulfonic acid) (10 mM), supplemented, as reported by Di Porzio U. et al. (Nature 288:370, 1980), with insulin (25 μg/ml), transferrin (100 μg/ml), putrescine (60 μM), progesterone (20 nM), sodium selenite (30 nM), penicillin G (0.5 U/ml) and streptomycin (0.5 μg/ml); and containing T$_3$ (3,3',5'-triiodo-DL-thyronine) (30 nM) (Puymirat J. et al., Neuroscience 10:801, 1983). Typically, 2 ml of culture medium containing the desired number of dissociated cells were added to each dish. Identification of the cell types in vitro was carried out by indirect immunofluorescence utilizing monoclonal antibody RT97 against neurofilament proteins (Anderton B.H. et al., Nature 298:84, 1982), a specific indicator of neuronal cells in vitro, as reported by Doherty P. et al. (J. Neurochem. 42:1116, 1984). Briefly, the cultures were fixed for 7 minutes in methanol at −20° C. The fixed cultures were permeabilized by treatment for 30 minutes with 0.1% (vol/vol) of Triton X-100 (a polyoxyethylene ether) in PBS and then further incubated for 60 minutes with 10% fetal calf serum (FCS) containing PBS to block non-specific protein binding sites. Incubation with antineurofilament antibody (dilution 1:500) in PBS was carried out for 60 minutes at room temperature and was followed by 3 rinses with PBS containing 10% of FCS. Rhodamine-conjugated goat anti-mouse high affinity purified IgG (dilution 1:100) was then added to the culture for 60 minutes at room temperature and, after 3 rinses in PBS with 10% of FCS, coverslipped with glycerol/PBS (1:1) and examined in a Zeiss photomicroscope III equipped with rhodamine epifluorescence and phase contrast optics. Indirect immunofluorescence using mouse GFAP (Glial Fibrillary Acidic Protein) antiserum (to specifically label astrocytic cells in vitro) and goat antimouse high affinity purified rhodamine-conjugated IgG was conducted according to the procedure of Raff M. C. et al. (Brain Res. 174:283, 1979).

2. Method of Cell Survival Assessment With Time in Culture

Cell survival was assessed by morphological criteria (i.e. observation by phase contrast microscope of the number of surviving cells according to the time in vitro) together with biochemical evaluation of DNA content and the number of surviving dopaminergic cells per dish according to the time in vitro. The DNA content was established according to the method reported by Erwin B. G. et al. (Anal. Biochem. 110:291, 1981) while the number of dopaminergic cells per dish was determined after specific dopamine uptake and visualization of fluorescent neurons according to the method of glyoxylic acid-induced fluorescence (GIF) described by Bolstad G. et al. (Comp Biochem. Physiol. 62:61, 1979). For the latter purpose, the cells were observed with a Zeiss photomicroscope III equipped for catecholamine epifluorescence and phase contrast optics. Utilizing prefixed coordinates the number of GIF positive neurons corresponding to at least 3% of the total surface area was counted.

3. Method of Specific Dopamine and GABA Uptake Assessment

Assessment of specific $^3$H-dopamine uptake was carried out as described by Berger B. et al. (Neuroscience 7:193, 1982). The cells were washed once with preheated PBS supplemented with glucose (5 mM), CaCl$_2$ (1 mM), MgSO$_4$ (1 mM), ascorbic acid (0.1 mM), pargyline (0.1 mM) and preincubated for 5 minutes with 0.8 ml of the above solution. When necessary, benztropine (5 μM), desmethylimipramine (5 μM) or fluoxetine (1 μM) were added to the incubation medium. Routinely, 0.2 ml of $^3$H-dopamine (50 nM final concentration, S.A. (specific activity) 22–33 Ci/mmol, was then added and incubation continued for 15 minutes at 37° C. Uptake was stopped by removing the incubation mixture followed by 4 rapid rinses with ice cold PBS. $^3$H-dopamine was then extracted from each dish twice (15 minutes each) with 0.5 ml of 0.4M HClO$_4$ plus absolute ethanol (3:1, v/v). Recovery was over 95%. Radioactivity was assessed after addition of 10 ml of Instagel II (a liquid scintillation counting fluid) using a Packard TriCarb scintillation counter (Model 460 C). In separate samples at the end of incubation and washings, intracellular radioactivity was extracted with 0.5 ml of perchloric acid (0.4N) and analysed with high pressure liquid chromatography (HPLC) (Kotake C. et al., J. Neurosci. 2:1307, 1982; Shum A. et al., J. Chromatog. 228:123, 1982). Over 95% of the injected radioactivity was associated with the fraction gathered at the dopamine retention time.

Specific uptake assessment of $^{14}$C-GABA was tested as described by Prochiantz A. et al. (Nature 293:570, 1981), with addition of 0.1 μM of $^{14}$C-GABA (225 mCi.nmol) for 15 minutes at 37° C. Aminooxyacetic acid (10 μM) was used to prevent GABA catabolism. The GABA uptake inhibitor, diaminobutyric acid ($10^{-3}$M), was added when necessary. The washing and extraction procedures are those described for the studies of $^3$H-dopamine uptake. GABA identification was carried out by TLC (thin layer chromatography), (Lasher R. S., Brain Res. 69:235, 1974). Over 90% of the radioactivity was associated with a spot comigrating with authentic GABA.

Figure 4:
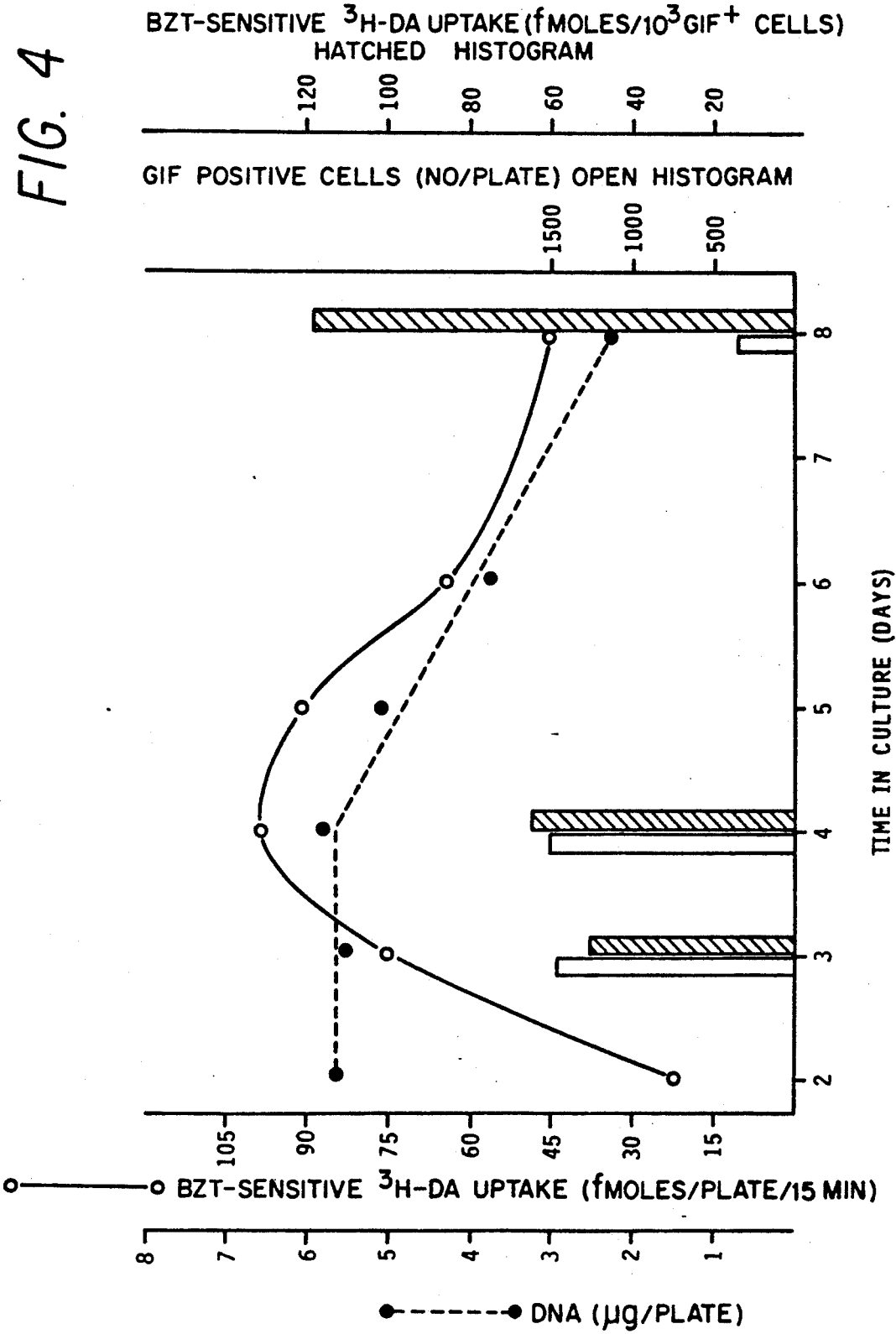
FIG. 4 is a graph showing time-related variations of total neurons, positive GIF neurons and BZT-sensitive dopamine uptake.

4. Morphological Assessment, Vitality and Biochemical Characteristics of the Cell Culture System At both 4 and 8 days in vitro, over 98% of the adhering viable cells present on the dish were positively immunoreactive to immunocytochemical staining with monoclonal antibody RT97. Also, less than 1% of the cells in culture were, at all the times considered, immunoreactive to staining with GFAP (glial fibrillary acidic protein) antiserum. This indicates that over 98% of the cells in culture may be classified as neuronal elements. Visualization of the number of dopaminergic neurons in the culture system indicated that these cells were approximately 0.1-0.2% of the total cell population present in vitro. Viability of the cells in the culture system used was unmodified up to 4 days in vitro. However, between 4 and 8 days in vitro the viability decreased by about 60-80%. This was clear not only after morphological assessment but also following assessment of DNA content and the number of dopaminergic cells per dish. This indicates that the viability of the mesencephalic neuronal cells in the culture conditions used was limited and that no notable variations occur in viability of the different cell types present in the culture system (see FIG. 4). FIG. 4 is a graph showing time-related variations of total neurons, positive GIF neurons and benztropine mesylate-sensitive (BZT-sensitive). dopamine uptake. The mesencephalic cells were seeded at a density of $1 \times 10^6$ cells/35 mm dish/2 ml of culture medium.

The indications on FIG. 4 are as follows: DNA/dish ( ); BZT-sensitive dopamine uptake ( ); number of GIF+ cells/dish (block histograms); BZT-sensitive dopamine uptake/ $10^3$ GIF+ cells (broken line histograms).

Similarly to determination of cell viability in culture, specific uptake of $^3$H-dopamine and $^{14}$C-GABA decreased by about 60-80% between the fourth and the eighth day in vitro. This again suggests that there is no apparent difference in behaviour between the various cell types present in vitro and infers that these uptake parameters are suitable indicators of cell viability in vitro.

Figure 5A:
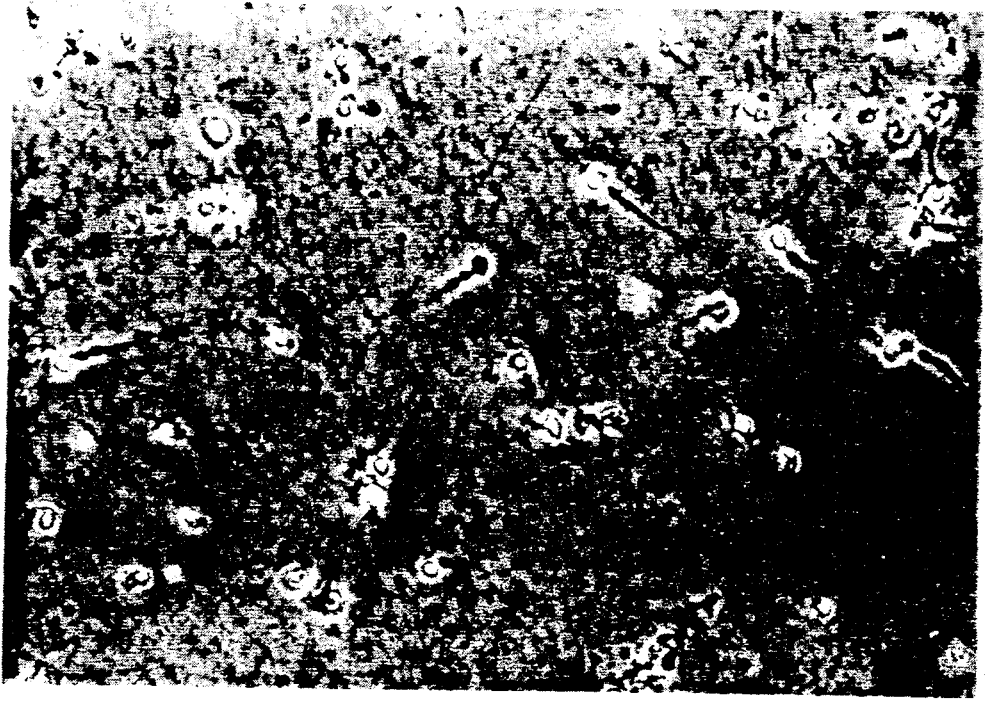
FIG. 5a is a microscopical view of the morphological appearance of fetal mouse mesencephalic cells in control test.
Figure 5B:
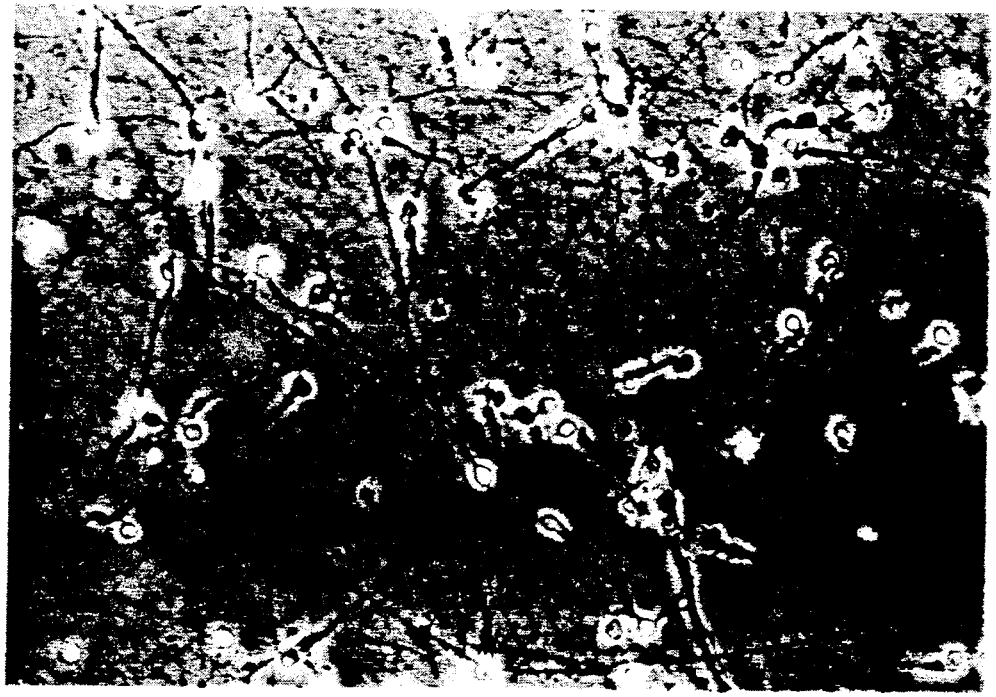
FIG. 5b is a microscopical view of the morphological appearance of fetal mouse mesencephalic cells on the eighth day after addition of active fraction.

5. Biological Activity of the Material Derived From the Major Stages of the Purification Procedure For this purpose, immediately before use, aliquots of the freeze-dried material derived from the major stages of purification were resuspended in 1/10 of the initial volume using distilled water. The protein content was evaluated according to Peterson G. L. (Anal. Biochem. 83:346, 1977). The samples were then diluted in culture medium, filtered through Millex 0.45 micron filters, and presaturated in bovine serum albumin (1 mg/ml). Suitable quantities of filtered material were then added to the mesencephalic cell culture on the day of plating. Equivalent quantities of bovine albumin were also added to the control cell cultures. In all cultures, the medium was substituted every two days or alternatively resupplemented with material derived from the purification stages or with albumin in the case of control cultures. The material derived from all the major purification stages—the raw supernatant extract obtained after acid precipitation of the total homogenate, the fractions obtained from the Sephadex G-150 column eluting in the molecular weight range of 10 to 30 kilodaltons and the fractions obtained from the TSK-CM-3SW column eluted at about 1M ammonium acetate—are all capable of increasing viability, that is survival and development, of dissociated fetal mesencephalic neuronal cells in culture. The morphological appearance on the eighth day of the cell cultures in vitro after addition to the culture medium on the day of plating, (day 0), of either the raw supernatant fraction or albumin (control culture) is shown in FIGS. 5A and 5B. These figures illustrate the typical appearance of the fetal mouse mesencephalic cells on the eighth day in vitro after addition of 10 $\mu$g/ml of albumin in the control culture (FIG. 5A) and 10 $\mu$g/ml of supernatant extract obtained following acid precipitation and dialysis of the total homogenate (FIG. 5B).

Figure 6:
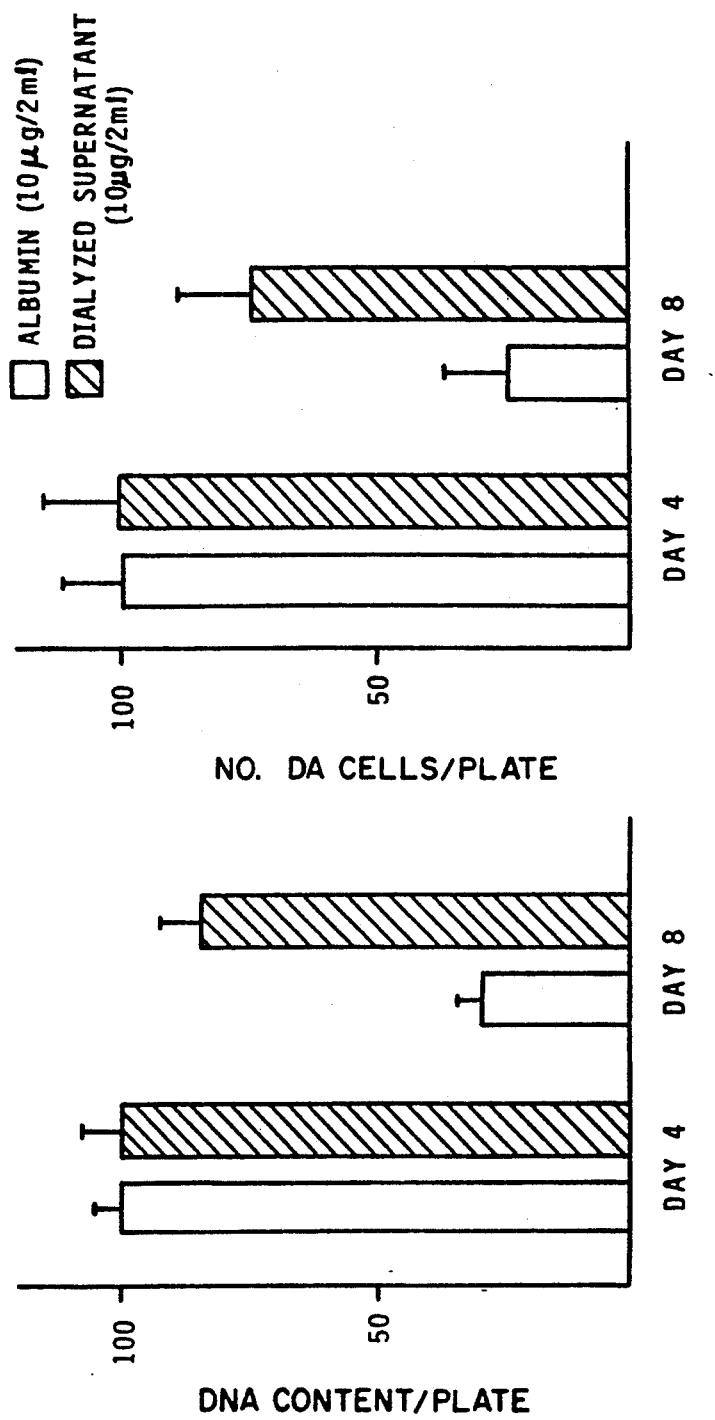
FIG. 6 is a bar graph showing the effect of dialyzed supernatent on DNA content and the number of DA cells with time in culture.
Figure 7:
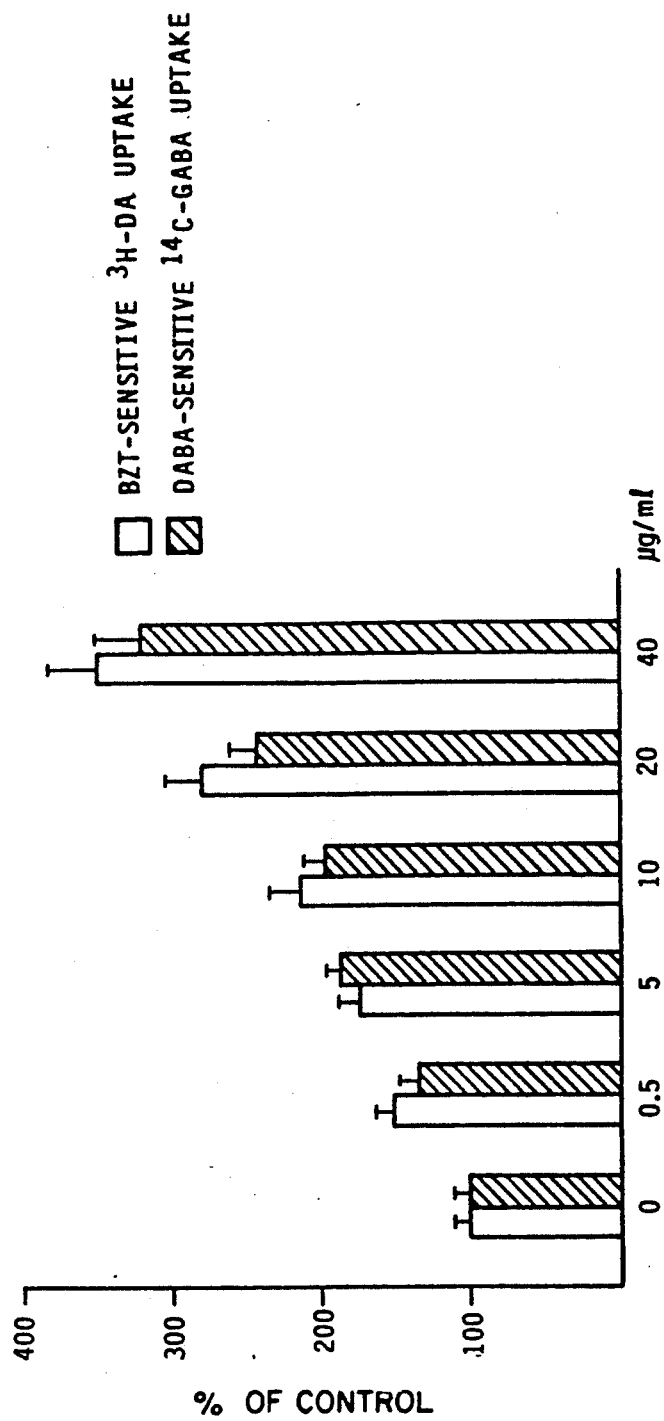
FIG. 7 is a graph showing the effect of dialyzed acid precipitated supernatent from caudate nucleus on specific uptake parameters in mesencephalic cell cultures.

This effect was evident also from a determination of the total DNA content and of the number of dopaminergic cells per dish (FIG. 6), and also specific uptake of $^3$H-dopamine and of $^{14}$C-GABA in terms of time in vitro. FIG. 6 shows an evaluation of the number of GIF+ cells (i.e. DA dopaminergic) and of DNA content per dish on the eighth day in vitro after addition of 10 $\mu$g/ml albumin to the control culture (block histograms) and 10 $\mu$g/ml of supernatant obtained following acid precipitation and dialysis of the total homogenate (broken line histograms). The control culture contained $1 \times 10^6$ mesencephalic cells plated/dish/2 ml culture medium. Values are mean values ±S.E. (standard error of the mean) of triple analyses. FIG. 7 shows that the effect of the above supernatant on dopamine uptake depends on concentration. This fact was observed from determination of GABA and DNA uptake per dish. Specifically, FIG. 7 shows the effect of the addition of various concentrations of bovine extract (obtained following acid precipitation and dialysis of the total homogenate) on BZT-sensitive dopamine uptake. Mesencephalic cells were seeded at a density of $0.5 \times 10^6$ cells/1 ml of culture medium/pool (24 mm). The indicated quantities of bovine extracts were added at plating time in a volume of 50 $\mu$l. When necessary, the samples were supplemented with bovine serum albumin so as to reach final concentrations of 40 $\mu$g/ml of protein. Uptake parameters were estimated on the fourth day in vitro. Values are reported as mean ±S.D. (standard deviation) of triplicated samples. Together, these results indicate that the active material is capable of enhancing survival and development in vitro of various neuronal types, in particular those present in the cultures used. Although similar effects were detected when testing for trophic activity in the supernatant extract, in the pool of Sephadex G-150 fractions eluted between 10 and 30 kilodaltons and in the group of fractions of the TSK-CM-3SW column eluted using about 1M of ammonium acetate, the quantity of material necessary for these effects differed. In particular, while the raw supernatant extract showed a semimaximal biological activity when added in vitro at concentrations of about 6 $\mu$g/ml, the semimaximal activity in the fractions obtained from Sephadex G-150 and TSK-CM-3SW column was detectable at about 0.3 $\mu$/ml and 10 ng/ml, respectively (see Table 1). The test for biological activity in other types of neuronal cell culture in vitro, in particular dissociated neuronal cells from fetal mouse striatum, indicated that the active molecule was effective in enhancing survival and development of various neuronal types present in different areas of the nervous system, in particular the central nervous system (CNS). Furthermore, the active material was effective in increasing neuritic growth in vitro of dorsal root ganglia neurons from 12-day embryo chicks but not of those from 8-day embryos. This effect indicates again that the neuronotrophic factor may be distinguished from β-NGF derived from mouse salivary glands. Indeed, the addition of various concentrations (from 1 ng to 300 ng/ml) of β-NGF from mouse salivary glands has no effect on survival of routinely used mouse dissociated mesencephalic cells in culture.

IV. In Vivo Application of the Neuronotrophic Factor Derived From Mammalian Brain Another object of the present invention concerns the in vivo application of the neuronotrophic factor (SDNF) derived from mammalian brain. As already discussed above, neuronotrophic factors are now known to regulate survival of neuronal cells and neuronal plasticity (defined as the ability of a nerve cell to undergo morphofunctional modifications in response to changes in its microenvironment) not only during development of the nervous system but also presumably in the adult state. Indeed, evidence is now being accumulated suggesting that neuronotrophic factors probably control adult neurons with regard to:

I. Maintenance, functional performance and aging of normal cells (Varon S., Discussions in Neuroscience, vol. II, No. 3, 1985)—that is, there must be a sufficient supply and usage of neuronotrophic factors to match normal variations of trophic needs and hence abnormal performance of adult neurons in vivo may reflect an inadequate support by trophic agents.

II. Repair and regeneration processes in chemically or mechanically lesioned cells (Varon S., ibid), in particular axonal lesion leads to a deficient supply of neuronotrophic factors to the neuronal cells and neuronal cell death is known to follow traumatic or pathological lesion and may be involved in the aging process.

III. Degeneration and death in some pathological conditions (Varon S., ibid), that is, different pathological conditions may be associated with situations of deficiency and may result in or be due to trophic deficits deriving either from a decline in effective trophic support or a rise in trophic needs or both.

In view of the above, the present invention is also directed to the following applications of the neuronotrophic factor known as SDNF, in particular, parenteral administration (including, although not exclusively, peridural, intracisternal, intraventricular, intrathecal, intravenous, intramuscular, subcutaneous, gingival, sublingual, rectal and nasal) of the SDNF molecule either alone or in association with gangliosides (in particular, mixtures of bovine brain gangliosides, single ganglioside species from bovine brain, preferably $GM_1$, and semisynthetic ganglioside derivatives, preferably derivatives of ganglioside internal esters), or phopholipids (in particular, mixtures of bovine brain phospholipids, species of single bovine brain phospholipids, preferably phosphatidylserine, and semisynthetic phospholipid derivatives), in neuropathological conditions deriving from:

I. Acute, subacute, or chronic injury to the nervous system, including traumatic injury, chemical injury, vasal injury and deficits (such as stroke), together with infectious/inflammatory and tumor-induced injury;

II. Aging of the nervous system including Alzheimer's disease;

III. Chronic neurodegenerative diseases of the nervous system, including Parkinson's disease, Huntington's chorea and amylotrophic lateral sclerosis;

IV. Chronic immunological diseases of the nervous system or affecting the nervous system, including multiple sclerosis.

Association of the use of the SDNF molecule with gangliosides and phospholipids is substantiated by evidence indicating that bovine brain gangliosides and bovine brain phospholipids are known to potentiate cellular responses to neuronotrophic factors in vitro and most probably in vivo.

The following table describes the effect of $GM_1$ and bovine striatal extract on mesencephalic cell cultures:

TABLE 2

| Substance | BZT-sensitive $^3$H-DA uptake fmol/plate 15 mins | DABA (diaminobutyric acid)-sensitive. $^{14}$C-GABA uptake pmol/plate 15 mins |
|---|---|---|
| Albumin | 29.51 ± 5.78 | 0.56 ± 0.14 |
| Albumin + $GM_1$ | 69.14 ± 3.38 | 1.04 ± 0.05 |
| Striatal extract | 104.68 ± 7.60 | 2.41 ± 0.27 |
| Striatal extract +GM1 | 140.58 ± 17.82 | 4.56 ± 0.10 |

Mescencephalic cells (1 × 10$^6$/plate) were cultivated in a serum-free medium containing albumin (15 μg/ml) or striatal extract (15 μg/ml), alone or in the presence of 10$^{-7}$M $GM_1$. Uptake studies were evaluated on the 4th day according to the methods reported in section IIIc. Values are mean ± s.e. of triple analysis. The bovine striatal extract was prepared as previously reported (see section IIIa).

a. Pharmaceutical Compositions

The formulation of pharmaceutical compositions containing the SDNF molecule derived from mammalian brain, described in this regard without and possibly also with gangliosides and phospholipids, includes known methods for the preparation of pharmaceutically acceptable compositions suitable for effective administration to the patient, by means of which an effective amount of the SDNF molecule is combined in admixture with a pharmaceutically acceptable vehicle. Suitable vehicles and their formulation inclusive of other proteins are described, for example, in the book "Remington's Pharmaceutical Sciences" (Remington's Pharmaceutical Sciences. Mack Publishing Company, Easton, Pa., USA 1985). These vehicles include injectable "deposit formulations". Based on the above, the pharmaceutical formulation includes, although not exclusively, SDNF solutions or a freeze-dried powder of SDNF in association with one or more pharmaceutically acceptable vehicles or diluents, and contained in buffered media at a suitable pH and isosmotic with physiological fluids. Table 3 below shows, for illustrative purposes only and without being limited by the same, the possible composition of formulations which may be prepared in the form of solutions for the treatment of nervous sytem disorders. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of the SDNF molecule in isotonic solutions of the desired volume and include, but not exclusively, the use of buffered saline solutions with phosphate or citrate at suitable concentrations so as to obtain at all times isotonic pharmaceutical preparations of the desired pH, for example, neutral pH. For illustrative purposes again, Tables 4A and 4B show some possible pharmaceutical compositions for the treatment of nervous system disorders. The pharmaceutical compositions set out in Tables 4A and 4B are preparations with two vials per single dose. The first vial contains the active substance with a composition by weight of about 0.01% to 50% of active substance together with a pharmacologically acceptable excipient, such as glycine or mannitol. The second vial contains a solvent prepared with the desired volume of phosphate or citrate buffered saline solution. The contents of the two vials are mixed immediately before administration and the freeze-dried active substance dissolves rapidly to obtain an injectable solution. Table 4B also shows a possible example of a pharmaceutical composition for subcutaneous injection (System No. 5). The pharmaceutical formulation also includes, but without being limited to the same, suppositories for rectal administration with lipophilic, i.e., hydrosoluble, autoemulsive excipients of glyco-gelatine or other types. In these preparations the SDNF may be present in quantities varying between 0.001% and 1% by weight of the whole excipient. The suppository forms may also contain, without being limited to the same, suitable quantities of acetyl-salicylate. Table 5 lists, for illustrative purposes only, possible suppository preparations for treatment of nervous system disorders. Furthermore, the pharmaceutical preparations of SDNF both in freeze-dried form and as solutions may include phospholipids or gangliosides as discussed above in effective doses. For example, the doses may be (albeit not exclusively) similar to those generally used in man for the treatment of nervous repair or complaints due to aging, respectively, and may depend on the administration route. The dosage of pharmaceutical preparations of SDNF and timing of administration depend on the effect desired (determined by clinical trials) and the administration route, for example, the dosage and timing of administration may be similar (albeit not exclusively) to that commonly used in studies with other neuronotrophic agents, such as NGF.

TABLE 3

EXAMPLES OF PHARMACEUTICAL COMPOSITIONS FOR INJECTABLE SOLUTIONS

| PREPARATION No. 1 - one 2 ml ampoule contains: | | |
|---|---|---|
| Active substance | μg | 5 (500 TU) |
| Sodium chloride | mg | 16 |
| Citrate buffer pH = 7 | ml | 2 |
| in apyrogenic distilled water q.b. | | |
| PREPARATION No. 2 - one 2 ml ampoule contains: | | |
| Active substance | μg | 100 (10,000 TU) |
| Sodium chloride | mg | 16 |
| Citrate buffer pH = 7 | ml | 2 |
| in apyrogenic distilled water q.b. | | |

The trophic unit (TU) is defined as in Table 1.

TABLE 4A

EXAMPLES OF PHARMACEUTICAL COMPOSITION SYSTEMS

| SYSTEM No. 1 | | |
|---|---|---|
| a) One 2 ml vial contains: | | |
| Freeze-dried active substance | μg | 5 (500 TU) |
| Glycine | mg | 30 |
| b) One 2 ml vial of solvent contains: | | |
| Sodium chloride | mg | 16 |
| Citrate buffer in water | ml | 2 |
| apyrogenic distilled water q.b. | | |
| SYSTEM No. 2 | | |
| a) One 2 ml vial contains: | | |
| Freeze-dried active substance | μg | 5 (500 TU) |
| Mannitol | mg | 40 |
| b) One 2 ml vial of solvent contains: | | |
| Sodium chloride | mg | 16 |
| Citrate buffer in water | ml | 2 |
| apyrogenic distilled water q.b. | | |
| SYSTEM No. 3 | | |
| a) One 3 ml vial contains: | | |
| Freeze-dried active substance | μg | 100 (10,000 TU) |
| Glycine | mg | 45 |
| b) One 3 ml vial of solvent contains: | | |
| Sodium chloride | mg | 24 |
| Citrate buffer in water | ml | 3 |
| apyrogenic distilled water q.b. | | |

The trophic unit (TU) is defined as in Table 1.

TABLE 4B

EXAMPLES OF PHARMACEUTICAL COMPOSITION SYSTEMS

| SYSTEM No. 4 | | |
|---|---|---|
| a) One 3 ml vial contains: | | |
| Freeze-dried active substance | μg | 100 (10,000 TU) |
| Mannitol | mg | 60 |
| b) One 3 ml vial of solvent contains: | | |
| Sodium chloride | mg | 24 |
| Citrate buffer in water | ml | 3 |
| apyrogenic distilled water q.b. | | |
| SYSTEM No. 5 (Example for subcutaneous injection) | | |
| a) One 2 ml vial contains: | | |
| Freeze-dried active substance | μg | 10 (1,000 TU) |
| Glycine | mg | 30 |
| b) One 2 ml vial of solvent contains: | | |
| Sodium chloride | mg | 16 |
| Citrate buffer in water | ml | 2 |
| apyrogenic distilled water q.b. | | |

The trophic unit (TU) is defined as in Table 1.

TABLE 6

Effect of basic FGF on specific dopamine and GABA uptake in mesencephalic cell cultures.

| | $^3$H-dopamine uptake | $^{14}$C-GABA uptake |
|---|---|---|
| Control | 100% | 100% |
| bFGF: 0.3 ng/ml | 693% | 233% |
| bFGF: 1 ng/ml | 972% | 285% |
| bFGF: 3 ng/ml | 1780% | 338% |
| bFGF: 10 ng/ml | 1880% | 363% |
| bFGF: 30 ng/ml | 2100% | 406% |
| bFGF: 100 ng/ml | 1850% | 404% |

Basic FGF

Recently, some work has been reported on basic mammalian fibroblast growth factors (FGF). Basic FGF has been purified from most mesoderm—and neuroectoderm—derived tissues, these having been shown to be FGF sensitive, either in vitro or in vivo. Such tissues include brain, pituitary, retina, corpus luteum, adrenal gland, kidney, prostate and thymus.

Sodium dodecylsulfate-polyacrylamide gel electrophoresis (SDS-PAGE) resolves the purest preparations of basic FGF into one or two very distinct bands with apparent molecular weights of 16,000 and 15,000 (Gospodarowicz D. et al., Proc. Natl. Acad. Sci. USA 81:6960, 1984). Structural studies have shown that basic FGF, as usually isolated, occurs as a single polypeptide chain of 146 amino acids. An amino terminal truncated form missing the first 15 amino acids—des 1-15 FGF—has also been reported (Esch F. et al., Proc. Natl. Acad. Sci. USA 82:6507, 1985). Depending on the organ from which it is purified, either the complete or truncated form of basic FGF can be present.

The truncated form of basic FGF is as potent as native FGF, thus indicating that the amino terminal FGF region is neither involved in biological activity nor in binding to FGF cell surface receptors. Basic FGF shows two potential binding domains for heparin, one being located near the amino terminal region, while the other is near the carboxyl terminus (residues 18-22 and 107-110, respectively). Basic FGF from both bovine and human sources has been sequenced. The molecule appears to have been highly conserved throughout evolution, as the bovine and human basic FGF species display 98.7% sequence homology.

Basic FGF has been extensively studied both in vitro and in vivo.

In vitro, addition of basic FGF to a culture medium is capable of affecting the proliferation and morphology of mesoderm-derived cells, as well as the survival and differentiation of neuronal and non-neuronal cells.

In vivo, basic FGF enhances limb and lens regeneration, survival of retinal ganglion cells after optic nerve section as well as wound healing and angiogenic activity.

Details concerning these studies can be found in the paper by Gospodarowicz et al., Endocrine Res. 8:95, 1987.

Comparison Between SDNF and Basic FGF

The biological characterization of SDNF shows that basic FGF possesses biological activity similar to SDNF. This indicates that basic FGF behaves biologically as an SDNF-like compound.

As previously mentioned, basic FGF possesses a molecular weight of 15 and 16 Kda. In addition, the truncated form of basic FGF, missing the first 15 amino acids, has a molecular weight of approximately 14 Kda. Furthermore, basic FGF has recently been reported to exert trophic effects (i.e. enhanced neuronal survival and neurite extension) in hippocampal as well as cerebral cortical neurons in vitro (Wallicke P. et al., Proc. Natl. Acad. Sci. USA 83:3012, 1986; Morrison R. S. et al., Proc. Natl. Acad. Sci. USA 83:7537, 1986). Therefore, in view of the similarity between the molecular weight ranges of basic FGF with SDNF, the aim of the following experiments was to ascertain whether basic FGF shared similar biological activity to SDNF. These comparative experiments were conducted utilizing cell culture systems (fetal dissociated mesesencephalic cells) known to respond to SDNF as well as cell culture systems (3T3 fibroblasts and pheochromocytoma PC12 cells) known to respond to basic FGF.

As previously discussed, in the fetal mesencephalic cell culture system, SDNF increases neuronal cell survival and specific neurotransmitter uptake in both the dopaminergic and GABAergic neurons present in the cultures. Utilizing this same culture system, Table 6 shows that basic FGF is capable of increasing in a dose-dependent manner both specific $^3$H-dopamine and $^{14}$C-GABA uptake, an effect indicative of an enhanced survival of at least the dopaminergic and GABAergic neurons present. In fact, when judged by morphological appearance of the cells at day 10 in vitro, it was clearly evident that the basic FGF increased overall cell survival of the mesencephalic cells. It is important to note that the dopaminergic neurons appear to be more sensitive to basic FGF than GABAergic neurons: at saturation (3 ng/ml) the dopamine uptake increased about 20-fold, while GABA uptake was increased about 4-fold.

Basic FGF is known to have proliferative effects when added to 3T3 fibroblasts (Gospodarowicz D. et al., J. Cell Physiol. 127:323, 1985) and to facilitate neurite extension when added to primed pheochromocytoma PC12 cells (Neufeld G. et al., J. Cell Physiol. 131:131, 1987). Thus, SDNF was applied to 3T3 fibroblasts and PC12 cells and its effects evaluated in terms of proliferation and neurite regeneration, respectively. Table 7 shows that in both cell types SDNF shares biological activity similar to basic FGF, thus confirming the previous result obtained with the mesencephalic cells.

In summary, it can be concluded that SDNF shares, at least on the culture system tested, biological characteristics similar to basic FGF. Thus another characteristic of SDNF is its similarity, in terms of biological effects, to basic FGF.

TABLE 6

Effect of basic FGF on specific dopamine and GABA uptake in mesencephalic cell cultures.

|  | $^3$H-dopamine uptake | $^{14}$C-GABA uptake |
| --- | --- | --- |
| Control | 100% | 100% |
| bFGF: 0.3 ng/ml | 693% | 233% |
| bFGF: 1 ng/ml | 972% | 285% |
| bFGF: 3 ng/ml | 1780% | 338% |
| bFGF: 10 ng/ml | 1880% | 363% |
| bFGF: 30 ng/ml | 2100% | 406% |
| bFGF: 100 ng/ml | 1850% | 404% |

Basic FGF was added at different concentrations at day 0. The uptake parameters were assessed at day 10 in vitro. Standard error was at all times less than 5% of the mean. The values are reported as % of control and are the mean of triplicate samples.

TABLE 7

|  | [$^3$H]TdR incorporation into DNA |
| --- | --- |
| 3T3 FIBROBLASTS | |
| Control | 100% |
| SDNF: 200 ng/ml | 900% |
| bFGF: 1 ng/ml | 1000% |

|  | % of process-bearing clumps |
| --- | --- |
| PC12 CELLS | |
| Control | 10% |
| SDNF: 300 ng/ml | 100% |

TABLE 7-continued

| bFGF: 10 ng/ml | 100% |
| --- | --- |

Notes to Table 7
Cell culture techniques
3T3 cells
Cells were plated into 6 mm diameter wells at 25,000 cells per well in Dulbecco's Modified Eagle's Medium (DMEM) + 10% fetal calf serum. After 4 hours, the cultures were washed and refed with DMEM. The following day the agents to be tested were presented in 100 l fresh DMEM.
DNA synthesis
To evaluate DNA synthesis, cultures of 3T3 cells were pulsed with 2 Ci/ml [methyl-$^3$H]thymidine for the last 2 hours of the treatment period. Cultures were subsequently washed with 5% trichloroacetic acid (TCA) to extract soluble [$^3$H]thymidine, and the acid precipitable radioactivity solubilized with 1N NaOH. The alkali extract was neutralized and counted.
PC12 cells
Cells were grown as described by Green L.A. and Tichler A.S. (Proc. Natl. Acad. Sci. USA 73:2424-2478, 1976). For regeneration experiments, NGF primed cells were used after 15 days with extensive neurite outgrowth. In brief, primed cells were washed extensively to remove NGF and replated onto new dishes in the presence of the agent to be tested. The dishes were then scored 24 hours later for the proportion of neurite-bearing clumps.

Verification of Biological Activity and Molecular Weight of SDNF

To date, several different preparations of SDNF have been obtained as previously exemplified. At all times, the biological activity and molecular weight of SDNF were routinely evaluated.

Whereas the biological characteristics of the different SDNF preparations were at all times the same, an approximately 20% to 30% difference in specific biological activity was found to occur upon comparison of the different preparations. In addition, analysis of the molecular weight utilizing SDS-PAGE electrophoresis of the different SDNF preparations showed that the molecular weight ranges within approximately 14,000 to 17,000 daltons (see FIG. 8 in the attached drawings). Such effects are perhaps due to the intrinsic variability of the purification and electrophoresis procedures as well as the cell culture system utilized.

Figure 8:
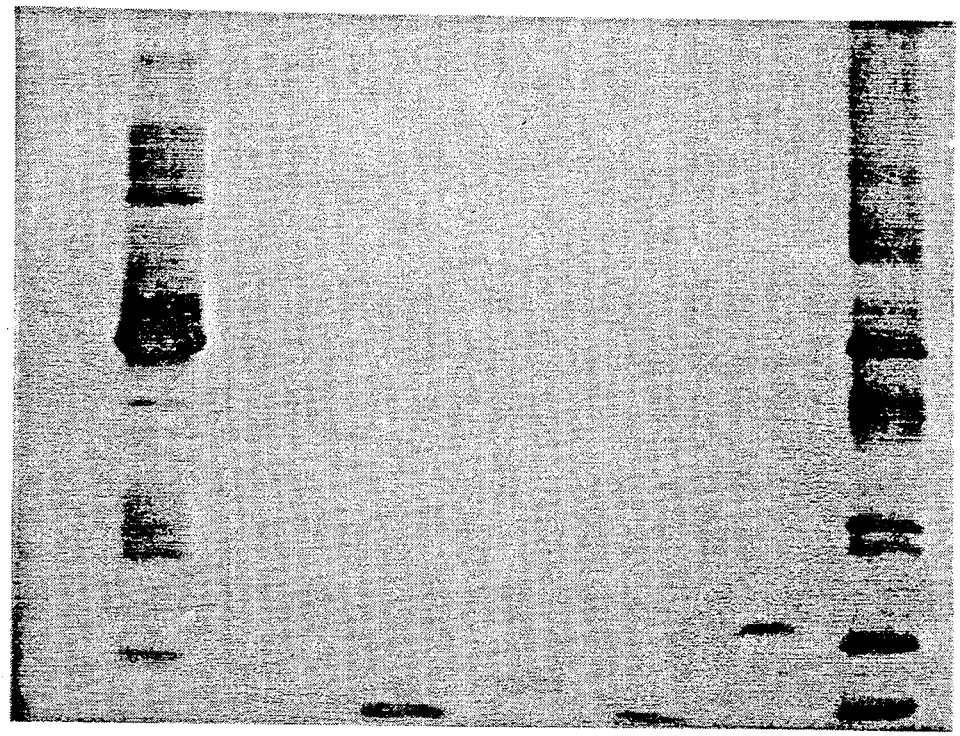
FIG. 8 shows the results of SDS-PAGE electrophoresis for analysis of the molecular weight of the different SDNF preparations.

FIG. 8 shows the SDS-PAGE electrophoresis of different SDNF preparations. From left to right the lanes which appear in this figure are as follows:
a. Molecular weight standard:
phospholipase b 94 Kd
albumin 67 Kd
ovalbumin 43 Kd
carbonic anhydrase 30 Kd
trypsin inhibitor 20.1 Kd
alfa-lactoalbumin 14.4 Kd
b. Murine NGF (beta subunit)
c. Bovine SDNF (code SDNF-23)
d. Bovine SDNF (code SDNF-35)
f. Bovine basic FGF (commercial source)

In summary, additional evidence indicates that the molecular weight of biologically active SDNF is in the range of 14,000 to 17,000 daltons.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A process for the preparation of a neuronotrophic factor which is a basic protein having a molecular weight of 14,000 to 17,000 Daltons as determined by SDS-PAGE and an isoelectric point of about 10 which comprises the steps of (a) homogenization of mammalian brain tissue, (b) acid precipitation of the homogenate thus produced, (c) dialysis of the resulting supernatant with a dialysis membrane having a molecular weight restriction of 5 to 10 kilodaltons, (d) chromatographic fractionation of the dialyzed supernatant to separate the supernatant components according to their molecular weight, and (e) purification of neuronotrophically active fractions obtained from step (d), as determined by dopamine uptake, by cation exchange CM-HPLC.

2. A process according to claim 1, wherein said CM-HPLC is conducted with a gradient of ammonium acetate buffer.

3. A process according to claim 1 or claim 2, wherein the mammalian brain tissue is bovine brain tissue.

4. A process according to claim 1 or claim 2, wherein caudate nuclei from bovine brains are subjected to said process steps.

5. A process according to claim 1, wherein step (b) is conducted at a pH of 4-5.

6. A process according to claim 1, wherein the chromatographic fractionation step (d) is carried out on a molecular sieve with a diluted buffered eluent at a concentration of 10 mM-30 mM.

7. A process according to claim 6, wherein the fractionation is carried out using a stationary phase with a fractionation range of 5,000 to 150,000 Daltons.

8. A process according to claim 2, wherein the neuronotrophically active fractions are purified by cation exchange CM-HPLC with a gradient of ammonium acetate buffer having a concentration of 0.1M to 1M and a pH of 6-7.

9. A process according to claim 1 or claim 2, wherein the process steps are conducted at a temperature of 0° to 6° C.

10. A process according to claim 1 or claim 2, wherein neuronotrophically active fractions obtained from step (d) are pooled together and freeze-dried.

11. A neuronotrophic factor prepared according to the process of claim 1.

12. A neuronotrophic factor prepared according to the process of claim 1, wherein the chromatographic fractionation in step (d) is conducted with Sephadex-G-150.

13. A neuronotrophic factor prepared according to the process of claim 2.

14. A neuronotrophic factor prepared according to the process of claim 2, wherein the cation exchange chromatography is conducted with an ammonium acetate buffer concentration of about 1M.

15. A neuronotrophic factor prepared according to the process of claim 1 or claim 2, which enhances survival and differentiation of neuronal cells.

16. A substantially pure neuronotrophic factor which is free of other proteins associated with bovine caudate tissues and which is a basic protein having a molecular weight of about 14,400 Daltons as determined by SDS-PAGE and an isoelectric point of about 10, wherein said neuronotrophic factor enhances the survival of nervous system neurons in culture.

17. The neuronotrophic factor according to claim 16, which has a specific activity of at least 0.01 µg/trophic unit, in which the aforesaid trophic unit is the protein concentration (µg/ml) which enhances survival of half the maximum number of neurons that survive in response to the saturating concentration of active material.

18. A substantially pure neuronotrophic factor which is free of other proteins associated with bovine caudate tissues and which is a basic protein derived from the mammalian brain caudate nucleus, said factor having a molecular weight of 14,000 to 17,000 Daltons as determined by SDS-PAGE, and an isoelectric point of about 10, wherein said neuronotrophic factor enhances the survival of nervous system neurons in culture.

19. The neuronotrophic factor according to claim 18, which has a specific activity of at least 0.01 μg/trophic unit, in which the aforesaid trophic unit is the protein concentration (μg/ml) which enhances survival of half the maximum number of neurons that survive in response to the saturating concentration of active material.

* * * * *